(12) United States Patent
Bateman et al.

(10) Patent No.: US 8,664,211 B2
(45) Date of Patent: Mar. 4, 2014

(54) MODIFIED AMINO ACID FOR THE INHIBITION OF PLATELET AGGREGATION

(75) Inventors: Simon David Bateman, Randolph, NJ (US); Moise Azria, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/327,129

(22) Filed: Dec. 15, 2011

(65) Prior Publication Data

US 2012/0088833 A1 Apr. 12, 2012

Related U.S. Application Data

(63) Continuation of application No. 12/169,184, filed on Jul. 8, 2008, now abandoned, which is a continuation of application No. 10/521,492, filed as application No. PCT/EP03/07739 on Jul. 16, 2003, now abandoned.

(60) Provisional application No. 60/396,898, filed on Jul. 17, 2002.

(51) Int. Cl.
*A61K 31/33* (2006.01)

(52) U.S. Cl.
USPC ............................................. 514/183

(58) Field of Classification Search
USPC ............................................. 514/183
See application file for complete search history.

(56) References Cited

U.S. PATENT DOCUMENTS

| 5,260,321 | A | * | 11/1993 | Hof et al. ................... 514/338 |
| 5,563,158 | A | | 10/1996 | Degrado et al. |
| 5,773,647 | A | | 6/1998 | Leipold et al. |
| 5,866,536 | A | | 2/1999 | Ho et al. |

FOREIGN PATENT DOCUMENTS

| WO | WO 00 59863 | 10/2000 |
| WO | WO 02 45754 | 6/2002 |

OTHER PUBLICATIONS

Leone-Bay et al., "Oral Deliverty of Biologically Active Parathyroid Hormone", Pharmaceutical Research, vol. 18, No. 7, pp. 964-970, (2001).

* cited by examiner

*Primary Examiner* — Brandon Fetterolf
*Assistant Examiner* — Christopher R Stone
(74) *Attorney, Agent, or Firm* — Ann R. Pokalsky, Esq.; Dilworth & Barrese, LLP

(57) ABSTRACT

A method of inhibiting blood platelet aggregation in a mammal is provided. The method comprises the administration of a platelet aggregation inhibiting amount of a modified amino acid or pharmaceutically acceptable salt thereof.

7 Claims, No Drawings

MODIFIED AMINO ACID FOR THE INHIBITION OF PLATELET AGGREGATION

This is application is a continuation of application Ser. No. 12/169,184 filed Jul. 8, 2008 which is a continuation of application Ser. No. 10/521,492 filed on Aug. 23, 2005, which is National Stage of International Application No. PCT/EP2003/07739 filed on Jul. 16, 2003, which claims the benefit of U.S. Provisional Application No. 60/396,898 filed on Jul. 17, 2002 the entire disclosures of which are hereby incorporated by reference.

Platelet activation and aggregation are involved in unstable angina and acute myocardial infarction, in reocclusion following thrombolytic therapy and angioplasty, in transient ischemic attacks and in a variety of other cardiovascular disorders. When a blood vessel is damaged either by acute intervention, such as angioplasty, or more chronically by the pathophysiological processes of atherosclerosis, platelets are activated to adhere to the damaged surface and to each other. This platelet activation, adherence and aggregation may lead to occlusive thrombus formation in the lumen of the blood.

Various agents have been studied for many years as potential targets for inhibiting platelet aggregation and thrombus formation. For example, aspirin has come into use as a prophylactic antithrombotic agent due its ability to inhibit platelet aggregation.

U.S. Pat. No. 5,773,647 ('647) and U.S. Pat. No. 5,866,536 ('536) describe compositions for the oral delivery of pharmacologically active agents with modified amino acids, such as N-(5-chlorosalicyloyl)-8-aminocaprylic acid (5-CNAC), N-(10-[2-hydroxybenzoyl]aminodecanoic acid (SNAD), and N-(8-[2-hydroxybenzoyl]amino)caprylic acid (SNAC). In addition, WO 00/059863 ('863) discloses the disodium salts of formula I

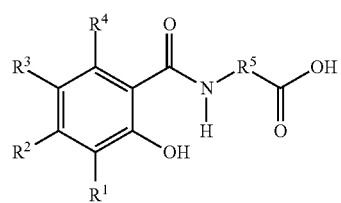

wherein
$R^1$, $R^2$, $R^3$ and $R^4$ are independently hydrogen, —OH, —$NR^6R^7$, halogen, $C_1$-$C_4$alkyl or $C_1$-$C_4$alkoxy;
$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
$R^6$ and $R^7$ are independently hydrogen, oxygen or $C_1$-$C_4$alkyl; and hydrates and solvates thereof as particularly efficacious for the oral delivery of active agents.

Surprisingly, it has now been discovered that the modified amino acids of '647, '536 and '863 are effective inhibitors of blood platelet aggregation. Thus, pharmaceutical compositions employing the modified amino acids of '647, '536 and '863 as carriers for pharmacologically active agents have the added advantage of inhibiting blood platelet aggregation.

Accordingly, the present invention provides a method of inhibiting platelet aggregation in a mammal, preferably human, comprising the administration of a platelet aggregation inhibiting amount of a modified amino acid, or a pharmaceutically acceptable salt thereof.

In another embodiment, the invention provides a method of inhibiting platelet aggregation in a mammal, preferably human, comprising the administration of a pharmaceutical composition comprising a platelet aggregation inhibiting amount of a modified amino acid or pharmaceutically acceptable salt thereof.

In an additional embodiment, the present invention provides a method of inhibiting platelet aggregation in a mammal, preferably human, receiving a pharmacologically active agent comprising the administration of a pharmaceutical composition comprising said pharmacologically active agent and a modified amino acid or a pharmaceutically acceptable salt thereof, wherein the modified amino acid or salt thereof is present in an amount effective to inhibit platelet aggregation.

The invention is furthermore concerned with a method of inhibiting platelet aggregation in a mammal (preferably human) comprising administering a platelet aggregation inhibiting amount of N-(-5-chlorosalicyloyl)-8-aminocaprylic acid (5-CNAC), or a pharmaceutically acceptable salt thereof, to said patient.

In an additional embodiment, the invention provides a method of inhibiting platelet aggregation in a mammal, preferably human, comprising the administration of a pharmaceutical composition comprising a platelet aggregation inhibiting amount of 5-CNAC or pharmaceutically acceptable salt thereof.

In a yet further embodiment, the invention provides a method of inhibiting platelet aggregation in a mammal, preferably human, receiving a pharmacologically active agent comprising the administration of a pharmaceutical composition comprising said pharmacologically active agent and 5-CNAC or pharmaceutically acceptable salt thereof, wherein the 5-CNAC or salt thereof is present in an amount effective to inhibit platelet aggregation.

It is to be understood that in embodiments of the invention comprising both a pharmacologically active agent and a modified amino acid, the platelet aggregation inhibition activity is a function of the modified amino acid. Such platelet aggregation activity is not a function of the pharmacologically active agent.

In an other embodiment, the invention provides a method of inhibiting platelet aggregation in a mammal receiving heparin, insulin, parathyroid hormone or calcitonin treatment, comprising administering a pharmaceutical composition comprising said heparin, insulin, parathyroid hormone or calcitonin and a modified amino acid, or pharmaceutically acceptable salt thereof, wherein the modified amino acid is present in an amount effective to inhibit platelet aggregation.

In an other embodiment, the invention provides a method of inhibiting platelet aggregation according to the invention, wherein the calcitonin is salmon calcitonin.

In an other embodiment, the invention provides a method of inhibiting platelet aggregation according to the invention, wherein the modified amino acid is present in an amount of about 25 mg to about 400 mg preferably in an amount of about 100 mg to about 200 mg.

In a further embodiment, the invention provides a method of inhibiting platelet aggregation according to the invention, wherein the pharmacologically active agent is present in an amount of 0.05% to 70% by weight relative to the total weight of the pharmaceutical composition.

In a further embodiment, the invention provides a method of inhibiting platelet aggregation in a mammal receiving heparin, insulin, parathyroid hormone or calcitonin treatment, comprising administering a pharmaceutical composition comprising said heparin, insulin, parathyroid hormone or calcitonin and 5-CNAC or pharmaceutically acceptable salt thereof, wherein the 5-CNAC is present in an amount effective to inhibit platelet aggregation.

In a further embodiment, the invention provides a method of inhibiting platelet aggregation according to the invention, wherein the pharmaceutical composition comprises calcitonin and 5-CNAC or a pharmaceutically acceptable salt thereof, and said mammal is human.

In a further embodiment, the invention provides a method of inhibiting platelet aggregation according to the invention, wherein the calcitonin is salmon calcitonin.

The present invention is directed to the use of a pharmaceutical composition comprising a platelet aggregation inhibiting amount of a modified amino acid, or a pharmaceutically acceptable salt thereof, for the manufacture of a medicament for the inhibition of platelet aggregation.

The invention also concerns the use of a pharmaceutical composition comprising a pharmacologically active agent and a modified amino acid, or pharmaceutically acceptable salt thereof, wherein the modified amino acid or salt thereof is present in an amount effective to inhibit platelet aggregation, for the manufacture of a medicament for the inhibition of platelet aggregation.

In a preferred embodiment the invention concerns the use of a pharmaceutical composition comprising a pharmacologically active agent and a modified amino acid, or pharmaceutically acceptable salt thereof, wherein the modified amino acid or salt thereof is present in an amount effective to inhibit platelet aggregation for the manufacture of a medicament for the inhibition of platelet aggregation said modified amino acid being N-(-5-chlorosalicyloyl)-8-aminocaprylic acid (5-CNAC), or a pharmaceutically acceptable salt thereof.

The invention also concerns the use of a pharmaceutical composition comprising heparin, insulin, parathyroid hormone or calcitonin and a modified amino acid, or pharmaceutically acceptable salt thereof, wherein the modified amino acid or salt thereof is present in an amount effective to inhibit platelet aggregation for the manufacture of a medicament for the inhibition of platelet aggregation in a mammal (preferably human) receiving heparin, insulin, parathyroid hormone (PTH) or calcitonin treatment.

In a preferred embodiment the invention concerns the use of a pharmaceutical composition according to the invention, wherein the calcitonin is salmon calcitonin.

In an other embodiment the invention concerns the use of a pharmaceutical composition according to the invention, wherein the modified amino acid is present in an amount of about 25 mg to about 400 mg.

In a preferred embodiment the invention concerns the use of a pharmaceutical composition according to the invention wherein the modified amino acid is present in an amount of about 100 mg to about 200 mg.

In an other preferred embodiment the invention concerns the use of a pharmaceutical composition according to the invention, wherein the pharmacologically active agent is present in an amount of 0.05% to 70% by weight relative to the total weight of the pharmaceutical composition.

The invention is also directed to the use of a pharmaceutical composition according to the invention wherein the pharmaceutical composition comprises calcitonin and 5-CNAC or a pharmaceutically acceptable salt thereof, and said mammal is human.

The invention is also directed to a pharmaceutical composition comprising a platelet aggregation inhibiting amount of a modified amino acid, or a pharmaceutically acceptable salt thereof for the inhibition of platelet aggregation.

The invention is furthermore directed to a pharmaceutical composition comprising a pharmacologically active agent and a modified amino acid, or pharmaceutically acceptable salt thereof, wherein the modified amino acid or salt thereof is present in an amount effective to inhibit platelet aggregation for the inhibition of platelet aggregation.

Further features and advantages of the invention will become apparent from the following detailed description of the invention and the appended claims.

A dose-inhibition experiment in platelet rich plasma (PRP) from 12 healthy subjects using 5 μM adenosine diphosphate (ADP) as platelet aggregation stimulator and various concentrations of 5-CNAC as platelet aggregation inhibitor was made. The platelet aggregation curves for three of the individual subjects stimulated by 5 μM ADP were established.

A dose-inhibition experiment was made in platelet rich plasma (PRP) from 12 healthy subjects using 5 μM adenosine diphosphate (ADP) as platelet aggregation stimulator and various concentrations of 5-CNAC as platelet aggregation inhibitor. Platelet aggregation curves for three of the individual subjects stimulated by 5 μM ADP were established.

A dose-inhibition experiment was made in PRP using 3 μM ADP as platelet aggregation stimulator and various concentrations of 5-CNAC as platelet aggregation inhibitor. The platelet aggregation curves for two of the individual subjects stimulated by 3 μM ADP were established.

A dose-inhibition experiment in PRP using 2 μM ADP as platelet aggregation stimulator and various concentrations of 5-CNAC as platelet aggregation inhibitor was made. The platelet aggregation curves for four of the individual subjects stimulated by 2 μM ADP were established.

A dose-inhibition experiment in PRP using 5 μg/mL collagen as platelet aggregation stimulator and various concentrations of 5-CNAC as platelet aggregation inhibitor was made. The platelet aggregation curves for two of the individual subjects stimulated by 5 μg/mL collagen were established.

A dose-inhibition experiment in PRP using 2.5 μg/mL collagen as platelet aggregation stimulator and various concentrations of 5-CNAC as a platelet aggregation inhibitor was made. The platelet aggregation curves for two of the individual subjects stimulated by 2.5 μg/mL collagen were established.

A dose-inhibition experiment in PRP using 2.0 μg/mL collagen as platelet aggregation stimulator and various concentrations of 5-CNAC as a platelet aggregation inhibitor was made. The platelet aggregation curve for the subject stimulated by 2.0 μg/mL collagen were established.

A dose-inhibition experiment in PRP using 1 μg/mL collagen as platelet aggregation stimulator and various concentrations of 5-CNAC as a platelet aggregation inhibitor was made. The platelet aggregation curves for the subjects stimulated by 1 μg/mL collagen were established.

A dose-inhibition experiment in PRP using 0.75 μg/mL collagen as platelet aggregation stimulator and various concentrations of 5-CNAC as a platelet aggregation inhibitor was made. A dose-inhibition experiment in PRP using 0.5 μg/mL collagen as platelet aggregation stimulator and various concentrations of 5-CNAC as a platelet aggregation inhibitor inhibitor was made. The platelet aggregation curves for the subjects stimulated by 0.5 μg/mL collagen were established.

The modified amino acids useful in the present invention include any one of the 123 modified amino acids disclosed in aforementioned '536 or any one of the 193 modified amino acids described in the aforementioned '647 or any combination thereof. The contents of the aforementioned '647 and '536 are hereby incorporated by reference in their entirety, especially the subject matter of the claims and corresponding working examples. In addition, the modified amino acids can be the disodium salt of any of the aforementioned modified amino acids as well as ethanol solvates and hydrates thereof. Suitable compounds include compounds of the following formula I

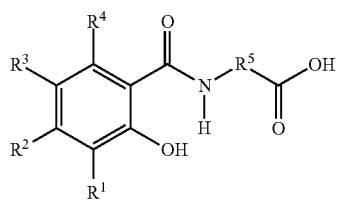

wherein
$R^1$, $R^2$, $R^3$ and $R^4$ are independently hydrogen, —OH, —$NR^6R^7$, halogen, $C_1$-$C_4$alkyl or $C_1$-$C_4$alkoxy;
$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
$R^6$ and $R^7$ are independently hydrogen, oxygen or $C_1$-$C_4$alkyl; and hydrates and alcohol solvates thereof. The compounds of formula I as well as their disodium salts and alcohol solvates and hydrates thereof are described in WO 00/059863, along with methods for preparing them.

The disodium salt may be prepared from the ethanol solvate by evaporating or drying the ethanol solvate by methods known in the art to form the anhydrous disodium salt. Drying is generally carried out at a temperature of from about 80° C. to about 120° C., preferably from about 85° C. to about 90° C., and most preferably at about 85° C. The drying step is generally performed at a pressure of 26" Hg or greater. The anhydrous disodium salt generally contains less than about 5% by weight of ethanol and preferably less than about 2% by weight of ethanol, based on 100% total weight of anhydrous disodium salt.

The disodium salt of the modified amino acid can also be prepared by making a slurry of the modified amino acid in water and adding two molar equivalents of aqueous sodium hydroxide, sodium alkoxide or the like. Suitable sodium alkoxides include, but are not limited to, sodium methoxide, sodium ethoxide and combinations thereof.

A still further method of preparing the disodium salt is by reacting the modified amino acid with one molar equivalent of sodium hydroxide to yield the disodium salt.

The disodium salt can be isolated as a solid by concentrating the solution containing the disodium salt to a thick paste by vacuum distillation. This paste may be dried in a vacuum oven to obtain the disodium salt of the modified amino acid as a solid. The solid can also be isolated by spray drying an aqueous solution of the disodium salt.

The modified amino acids may be prepared by methods known in the art, e.g., as mentioned above, by methods described in '647 and '536.

The ethanol solvates, as described in the aforementioned '863, include, but are not limited to, a molecular or ionic complex of molecules or ions of ethanol solvent with molecules or ions of the disodium salt of the modified amino acid. Typically, the ethanol solvate contains about one ethanol molecule or ion for every molecule of disodium salt of the modified amino acid.

The ethanol solvate of the disodium salt of the modified amino acid can be prepared by dissolving the modified amino acid in ethanol. Typically, each gram of modified amino acid is dissolved in from about 1 mL to about 50 mL of ethanol and generally, from about 2 mL to about 10 mL of ethanol. The modified amino acid/ethanol solution is then reacted with a molar excess of a sodium containing salt, such as a monosodium containing salt, relative to modified amino acid, i.e., for every mole of modified amino acid there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Preferably, at least about two molar equivalents of the monosodium containing salt are added to the ethanol solution, i.e., for every mole of modified amino acid there is at least about two moles of sodium cations. Generally, the reaction is performed at or below the reflux temperature of the mixture, such as at ambient temperature. The ethanol solvate is then recovered by methods known is the art, such as concentration of the resulting slurry at atmospheric distillation, cooling the concentrated slurry and filtering the solid. The recovered solid can then be vacuum dried to obtain the ethanol solvate.

The hydrates of the disodium salts of the modified amino acids may be prepared by drying the ethanol solvate to from an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture. Generally, the hydrating step is performed at from about ambient temperature to about 50° C., preferably ambient temperature to about 30° C. and in an environment having at least 50% relative humidity. Alternatively, the anhydrous disodium salt may be hydrated with steam.

The preferred modified amino acids are 5-CNAC, also known as 8-(N-2-hydroxy-5-chlorobenzoyl)aminocaprylic acid, SNAD, SNAC and their monosodium and disodium salts, ethanol solvates of their sodium salts and the monohydrates of their sodium salts and any combinations thereof. The most preferred modified amino acid is the disodium salt of 5-CNAC and the monohydrate thereof.

The pharmacologically active agents suitable for use in the instant invention include both therapeutic as well as preventative agents. The pharmacologically active agents include, but are not limited to proteins, polypeptides, hormones, polysaccharides including mixtures of muco-polysaccharides, carbohydrates, lipids and combinations thereof.

Specific examples of pharmacologically active agents include, but are not limited to the following, including synthetic, natural or recombinant sources thereof: growth hormone, including human growth hormones, recombinant human growth hormones, bovine growth hormones and porcine growth hormones; growth hormone-releasing hormones; interferons, including α, β and γ-interferon; interleukin-1; interleukin-2; insulin, including porcine, bovine, human and human recombinant, optionally having counter ions including sodium, zinc, calcium and ammonium; insulin-like growth factor, including IGF-1; heparin, including unfractionated heparin, heparinoids, dermatans, chondroitins, low, very low and ultra low molecular weight heparins; calcitonin, including salmon, porcine, eel, chicken and human; erythropoietein; atrial naturetic factor; antigens; monoclonal antibodies; somatostatin; protease inhibitors; adrenocorticotropin, gonadotropin releasing hormone; oxytocin; leutinizing-hormone-releasing hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine;

parathyroid hormone, including its fragments; antimicrobials, including anti-fungal agents; vitamins; analogs, fragments, mimetics or polyethylene glycol-modified derivatives of these compounds or any combination thereof.

A preferred pharmacologically active agent is a pharmacologically active peptide, particularly calcitonin. A known class of pharmacologically active agents, calcitonins have varying pharmaceutical utility and are commonly employed in the treatment of, e.g., Paget's disease, hypercalcemia and postmenopausal osteoporosis. Various calcitonins, including salmon, pig and eel calcitonin are commercially available and commonly employed for the treatment of, e.g., Paget's disease, hypercalcemia of malignancy and osteoporosis. The calcitonin can be any calcitonin, including natural, synthetic or recombinant sources thereof, as well as calcitonin derivatives, such as 1,7-Asu-eel calcitonin. The compositions can comprise a single calcitonin or any combination of two or more calcitonins. The preferred calcitonin is synthetic salmon calcitonin. The calcitonins are commercially available or may be synthesized by known methods.

Other preferred pharmacologically active agents are heparin, insulin and PTH.

The amount of pharmacologically active agent is generally an amount effective to accomplish the intended purpose, e.g., a therapeutically effective amount. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of active agent to be used can be determined by methods known to those skilled in the art. However, because the compositions may deliver the active agent more efficiently than prior compositions, less amounts of active agent than those used in prior dosage unit forms or delivery systems can be administered to a subject while still achieving the same blood levels and/or therapeutic effects.

When the pharmacologically active agent is salmon calcitonin, the appropriate dosage will, of course, vary depending upon, for example, the host and the nature and severity of the condition being treated. However, in general, satisfactory results will be obtained systemically at daily dosages of from about 0.5 µg/kg to about 10 µg/kg animal body weight, preferably 1 µg/kg to about 6 µg/kg body weight.

The pharmacologically active agent generally comprises from 0.05% to 70% by weight relative to the total weight of the overall pharmaceutical composition, preferably an amount of from 0.01% to 50% by weight, more preferably 0.3% to 30% by weight relative to the total weight of the overall pharmaceutical composition.

The pharmaceutical compositions for use in the present invention typically comprises a platelet-aggregation-inhibitory amount of one or more of the modified amino acids, i.e., an amount sufficient to inhibit blood platelet aggregation. Generally, the modified amino acid is present in a dosage range of between about 25 mg and about 400 mg. Most preferably the modified amino acid is present in a dosage range of between about 100 mg and about 200 mg.

The pharmaceutical compositions for use in the present invention typically comprises a pharmaceutically active agent and a platelet-aggregation-inhibitory amount of one or more of the modified amino acids, i.e., an amount sufficient to inhibit blood platelet aggregation.

The pharmaceutical compositions for use in the present invention may be provided as a capsule including a soft-gel capsule, tablet, caplet or other solid oral dosage form, all of which can be prepared by methods well-known in the art.

The pharmaceutical compositions for use in the present invention may additionally comprise additives in amounts customarily employed including, but not limited to, a pH adjuster; a preservative; a flavorant; a taste-masking agent; a fragrance; a humectant; a tonicifier; a colorant; a surfactant; a plasticizer; a lubricant, such as magnesium stearate; a flow aid; a compression aid; a solubilizer; an excipient; a diluent, such as microcrystalline cellulose, e.g., Avicel PH 102 supplied by FMC corporation; or any combination thereof. Other additives may include phosphate buffer salts, citric acid, glycols and other dispersing agents.

The pharmaceutical compositions for use in the present invention may optionally additionally comprise crospovidone, which can be any crospovidone. Crospovidone is a synthetic crosslinked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation.

Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP.

As mentioned above, the crospovidones and povidones are commercially available. Alternatively, they may be synthesized by known processes.

The crospovidone, povidone or combination thereof is generally present in the compositions in an amount of from 0.5% to 50% by weight relative to the total weight of the overall pharmaceutical composition, preferably an amount of from 2% to 25%, more preferably 5% to 20% by weight relative to the total weight of the pharmaceutical composition.

The pharmaceutical composition may also include one or more enzyme inhibitors, such as actinonin or epiactinonin and derivatives thereof; aprotinin, Trasylol and Bowman-Birk inhibitor.

Further, a transport inhibitor, i.e., a ρ-glycoprotein, such as Ketoprofin, may be present in the compositions of the present invention.

Preferably, the solid pharmaceutical compositions of the instant invention include a diluent, such as Avicel; and a lubricant, such as magnesium stearate.

The solid pharmaceutical compositions of the instant invention can be prepared by conventional methods, e.g., by blending a mixture of the active agent or active agents, the delivery agent and other ingredients, kneading and filling into capsules, or instead of filling into capsules, molding followed by further tableting or compression-molding to give tablets. In addition, a solid dispersion may be formed by known methods followed by further processing to form a tablet or capsule.

Preferably, the ingredients in the pharmaceutical compositions of the instant invention are homogeneously or uniformly mixed throughout the solid dosage form.

The pharmaceutical compositions of the present invention may be administered to deliver a pharmacologically active agent to any mammal in need thereof including, but not limited to, rodents, cows, pigs, dogs, cats and primates, particularly humans.

Experimental Procedures
Preparation of PRP (Platelet Rich Plasma)

Freshly drawn venous blood from healthy volunteers is collected into 0.1 vol. mmol/L trisodium citrate. The donors have not taken any medication during two weeks prior to blood collection. PRP is prepared by centrifugation of the freshly drawn blood (150 g, 15 minutes at 22° C.) and the final platelet concentration is standardized at 200 000 cell/µL by dilution in autologous platelet-free plasma, prepared by centrifugation (1200 g, 10 minutes at 22° C.). The supernatant is collected. Samples of PRP are pre-incubated for 1 minute (22° C.) with varying concentrations of 5-CNAC in saline (stored at −20° C.).

Platelet Aggregation Studies

In order to assess the inhibitory effect of 5-CNAC on platelet aggregation, the following studies are performed. Samples of 0.400 mL PRP containing 5-CNAC are prepared as above. To these samples is added 0.005 mL of an aggregation stimulator which is either ADP (Roche Molecular Biochemicals, Mannheim) or collagen (Horm Chemie, Munich). The final concentrations of either the ADP or collagen are as indicated in the "Results" section.

Aggregation studies are performed in a Chronolog 4 channel aggregometer (type CH570VS-CH810). The aggregometer automatically calibrates the donor-dependent difference in optical density between platelet-free plasma (0% optical density) and the PRP (100% optical density) of a particular donor. The extent of aggregation is measured by expressing the maximal difference in optical density (independent of the time after the addition of the aggregation stimulator, i.e., either ADP or collagen) and normalized taking the control curves (without 5-CNAC) as an internal standard set at 100%.

Results

Effect of 5-CNAC on Platelet Aggregation Induced by ADP

It is noted that the addition of 5-CNAC alone to PRP does not trigger platelet aggregation.

A dose-inhibition experiment was made in PRP from 12 healthy subjects using 5 µM ADP as the platelet aggregation stimulating agent and varying concentrations of 5-CNAC as the platelet aggregation inhibiting agent. Concentrations tested include 0.1, 1, 2, 5, 10, 25, 100, 200 and 500 µM It is seen that at increasing concentrations of 5-CNAC, inhibition of platelet aggregation becomes apparent at about 2 µM 5-CNAC or more. The aggregation curves of three individual subjects induced by 5 µM ADP were established. It is noted that 5 µM ADP stimulates maximal platelet aggregation.

In order to study the inhibitory effect of 5-CNAC at suboptimal ADP stimulation, studies were repeated with lower concentrations of ADP challenged by varying concentrations of 5-CNAC. A dose-inhibition study was made using 3 µM ADP. The corresponding aggregation curves for individual subjects were established. The same experiments using 2 µM ADP as the stimulator was made. The aggregation curves of individual subjects were established. The result showed that, as the concentration of the platelet aggregation stimulator (ADP) decreases, platelet aggregation is inhibited by lower concentrations of 5-CNAC. Moreover, it is observed that in all concentrations of ADP tested, the platelet aggregation inhibition by 5-CNAC is evident in the second phase of the aggregation curve, but is not observed in the initial phase of the aggregation curve. This effect is similar to integrin IIb 3 (glycoprotein IIb-IIIa) antagonists that interfere with platelet-platelet coupling.

Effect of 5-CNAC on Platelet Aggregation Stimulated by Collagen

Compared with ADP, collagen is a more potent platelet aggregation inducer. There is an adhesion phase in which platelets bind to the collagen insoluble fibers before becoming activated. The result shows that platelets are relatively resistant to aggregation inhibition when the platelets are stimulated by a high concentration of the aggregation stimulator collagen (5 µg/mL). Platelets are unaffected by 100 µM 5-CNAC. However, at about 1 mM 5-CNAC, inhibition of platelet aggregation becomes detectable.

Experiments were made at lower collagen concentrations (2.5 µg/mL) and showed that there is some inhibition of platelet aggregation by 200 µM 5-CNAC in the platelet rich plasma of one individual, but not at lower concentrations of the 5-CNAC At 2 µg/mL collagen, there is one individual showing platelet aggregation inhibition at about 1 mM 5-CNAC, while at a lower collagen concentration (1 µg/mL) inhibition by 5-CNAC is evident at 50 µM or more. Lower concentrations of the stimulator collagen reveal similar inhibition patterns by 5-CNAC. As with ADP-stimulated aggregation, the inhibitory effect of 5-CNAC on collagen-stimulated aggregation becomes apparent in the second phase of the aggregation curve, while no aggregation inhibition is observed in the primary aggregation curve. Also, when the concentration of collagen is lowered, the platelets become more sensitive to 5-CNAC inhibition.

Further observations include the following: i) 5-CNAC does not alter platelet morphology since the "swirling" of the cells remains intact; (ii) upon ADP addition there is an increase in optical density. This downward pattern is caused by a change in cell shape, which is a first response to platelet aggregation. This response is undisturbed in the presence of 5-CNAC; (iii) 5-CNAC dose-dependently inhibits the later part of the aggregation curve (also called secondary aggregation); (iv) the sensitivity of the PRP to 5-CNAC differs between subjects; and (v) the effect of 5-CNAC shows similarities with the inhibition by aspirin-like drugs that interfere with thromboxane $A_2$ production, or platelets from patients with a congenital secretion defect (so-called "storage pool deficiency").

As can be seen from the foregoing, modified amino acids of the instant invention are effective at inhibiting platelet aggregation.

What is claimed is:

1. A method of inhibiting platelet aggregation in a mammal, said method comprising: administering to a mammal with a cardiovascular disorder or a mammal having a blood vessel in reocclusion following thrombolytic therapy or following an acute intervention, a pharmaceutical composition consisting of N-(5-chlorosalicyloyl)-8-aminocaprylic acid (5-CNAC), or a pharmaceutically acceptable salt thereof, in an amount effective to inhibit platelet aggregation and at least one of a pH adjuster, a preservative, a flavorant; a taste-masking agent; a fragrance; a humectant; a tonicifier; a colorant; a surfactant; a plasticiser; a lubricant; a flow aid; a compression aid; a solubilizer; an excipient; a diluent; a phosphate buffer salt; citric acid, glycol, a dispersing agent, crospovidone, or povidone.

2. The method according to claim 1 wherein the 5-CNAC or pharmaceutically acceptable salt thereof is present in an amount of about 25 mg to about 400 mg.

3. The method according to claim 2, wherein the 5-CNAC or pharmaceutically acceptable salt thereof is present in an amount of about 100 mg to about 200 mg.

4. The method of claim 1 wherein the cardiovascular disorder is at least one of unstable angina, acute myocardial infarction, transient ischemic attack, or atherosclerosis.

5. The method of claim 1 wherein the acute intervention is angioplasty.

6. The method of claim 1 wherein the lubricant is magnesium stearate.

7. The method of claim 1 wherein the diluent is microcrystalline cellulose.

* * * * *